United States Patent [19]

Swain

[11] Patent Number: 5,780,720
[45] Date of Patent: Jul. 14, 1998

[54] OUTFLOW METER

[76] Inventor: Jon M. Swain, 3145 Holloway Rd., Ruston, La. 71270

[21] Appl. No.: 708,088

[22] Filed: Aug. 30, 1996

[51] Int. Cl.$^6$ ................................................ G01N 15/08
[52] U.S. Cl. ................................................................. 73/38
[58] Field of Search .............................. 73/38, 146, 306, 73/313, 319; 200/61.04

[56] References Cited

U.S. PATENT DOCUMENTS

| | | | |
|---|---|---|---|
| 4,164,139 | 8/1979 | Jones | 73/38 |
| 4,341,110 | 7/1982 | Block | 73/38 |
| 5,079,950 | 1/1992 | McKiernan et al. | 73/319 |

OTHER PUBLICATIONS

Outflow Meter Manual, Engineering Services Div. of Fed.Hwy. Admin. Sep. 1978.

*Primary Examiner*—Robert Raevis
*Attorney, Agent, or Firm*—John M. Harrison

[57] ABSTRACT

A self-contained outflow meter for resting on pavement and measuring the rate of water drainage from the pavement. The outflow meter includes a vertical tube for containing water and having a bottom water discharge end sealed by a rubber sealing ring. A spring-loaded plunger is suspended from a cap mounted on the upper end of the tube for selectively sealing a water discharge opening provided in the base. Upper and lower float switches are suspended from the cap into the tube and include upper and lower switch floats, respectively, which are vertically displaceably mounted. A timer is provided on the cap and is wired to the float switches. The base is placed on the pavement surface with the plunger sealing the water discharge opening and water is poured into the tube. As the water level exceeds the respective levels of the switch floats, the floats are displaced upwardly. The plunger is then released, allowing the water to flow from the tube through the discharge opening onto the pavement and under the sealing ring on the base. The floats are sequentially displaced by gravity and the timer records the elapsed time of water flow between the float switches and from the tube, thus indicating the rate of water drainage from the pavement.

4 Claims, 3 Drawing Sheets

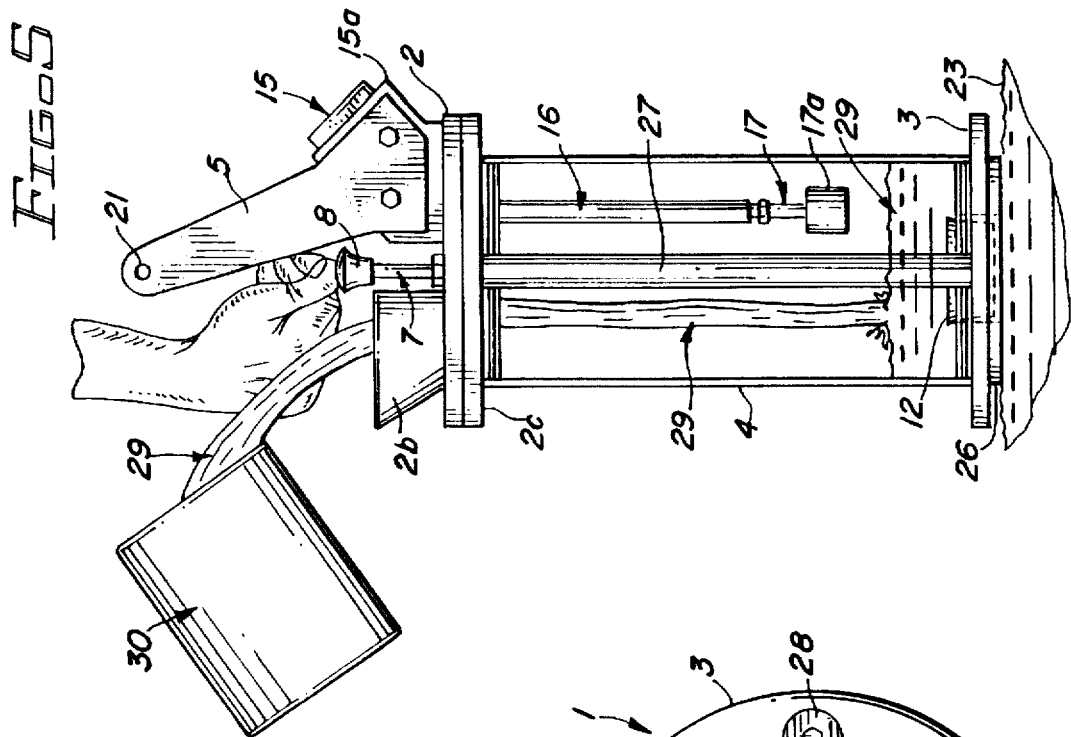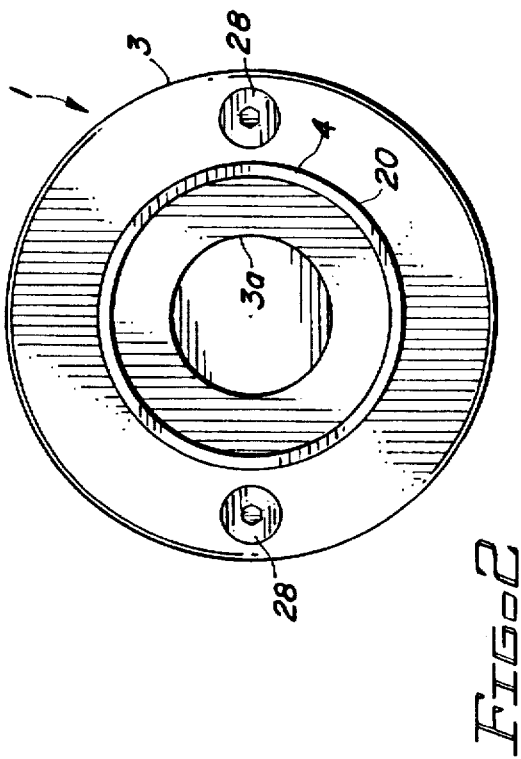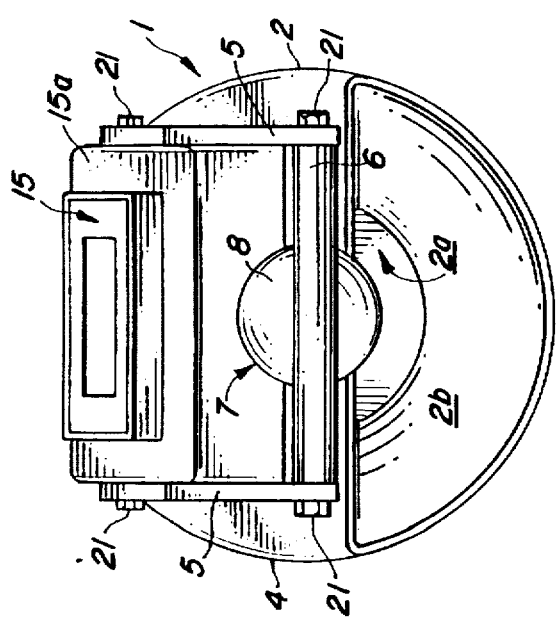

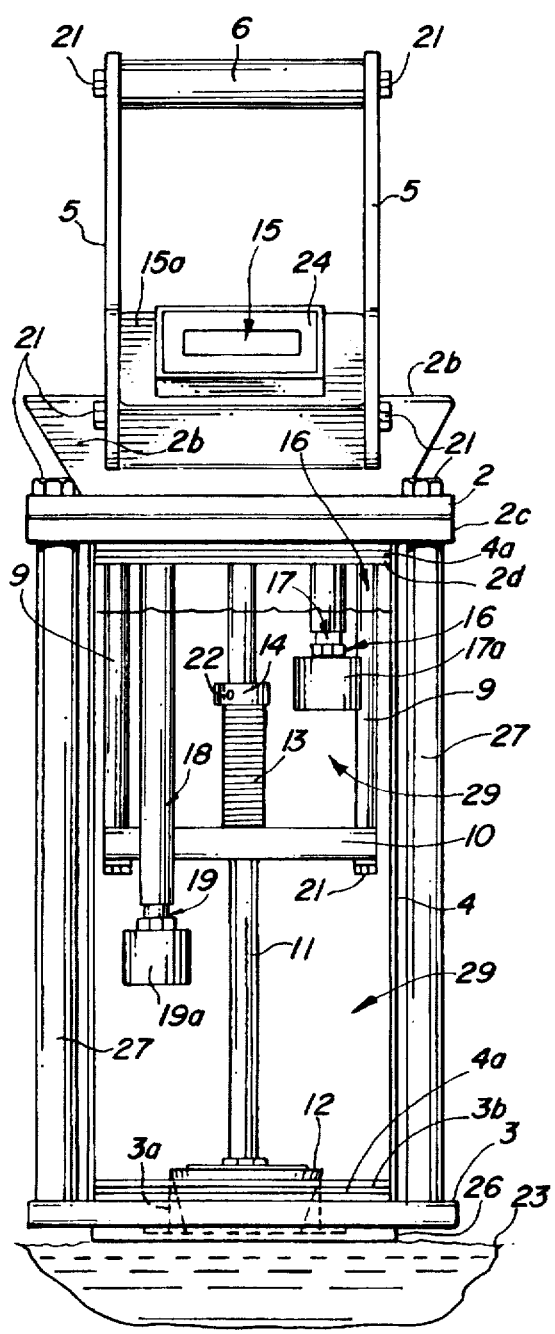
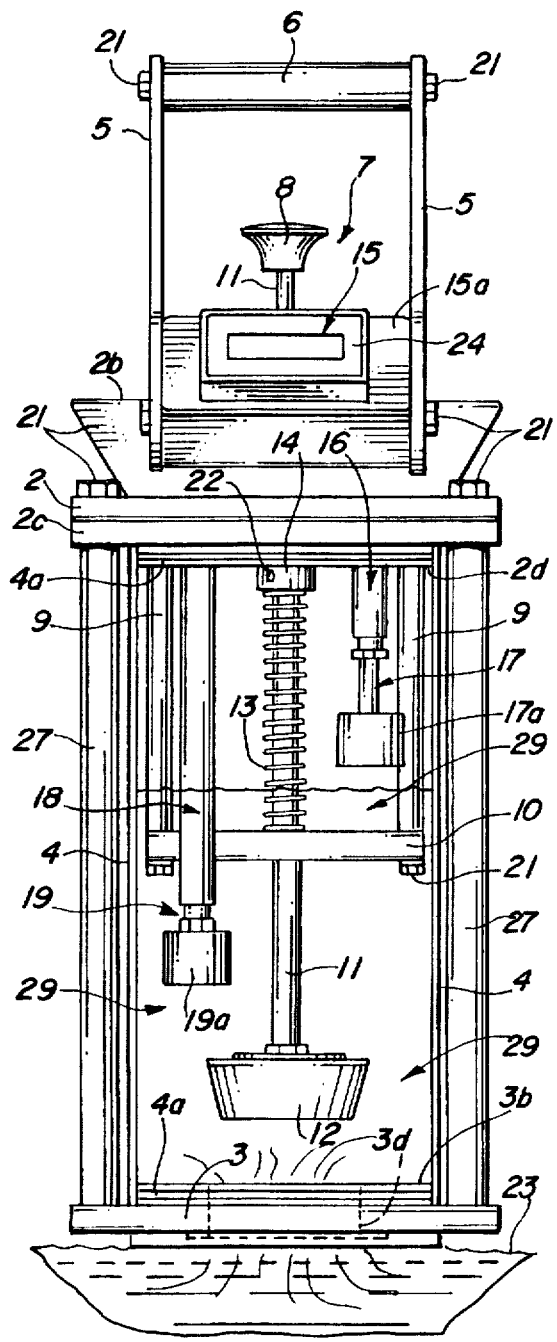

OUTFLOW METER

BACKGROUND OF THE INVENTION

1. Field of the Invention

This invention relates to devices for measuring the water drainage characteristics of pavement and more particularly, to a self-contained outflow meter for resting on pavement and measuring the rate of water drainage through the pavement texture. In a preferred embodiment the outflow meter is characterized by an elongated, cylindrical, vertically-oriented tube for containing water. A base is sealed in the bottom end and a cap in the top end of the tube, and a spring-loaded plunger is slidably suspended from the cap into the tube for selectively sealing a water discharge opening provided in the base. Upper and lower adaptors of different lengths are wired to an electronic timer provided on the cap and extend downwardly from the cap into the tube, the upper adaptor terminating in the upper portion and the lower adaptor in the lower portion of the tube. In a preferred embodiment, the float of a float switch is vertically and slidably mounted on the lower end of each adaptor. In application, the outflow meter is first placed on a pavement surface to be tested and the plunger operated to seal the discharge opening provided in the base. Water is then poured into the water discharge tube through an opening or funnel formed in the cap, to a level exceeding the level of the upper switch float. When the water is at this level, both the upper and lower switch floats are displaced into the raised or top position on the respective adaptors and this prevents the timer from operating. The timer is set and the plunger is then released to unseal the water discharge opening. As water flows from the tube through the discharge opening onto the pavement surface, the water level in the tube falls below the upper switch float, which is displaced downwardly by gravity on the upper adaptor, while the lower switch float remains in the upper position on the lower adaptor, causing the electronic timer to begin counting. As the water level continues to fall past the level of the lower switch float, the lower switch float is likewise downwardly displaced by gravity on the lower adaptor, and this causes the timer to stop counting. The time required for the water level in the tube to fall from the level of the upper float switch to the level of the lower float switch is indicated on the timer and indicates the rate of drainage of the pavement surface upon which the outflow meter is placed. This parameter, the main hydraulic radius of the surface texture of the pavement, indicates the drainage time of water from the pavement surface under the influence of a vehicle tire.

2. Description of the Prior Art

A typical conventional outflow meter is characterized by a vertical water discharge tube having a base and base seal for resting on the pavement surface, a cap mounted on the tube top and a plunger suspended from the cap for reversibly sealing a water discharge opening provided in the base. A pair of brass probes are typically suspended from the cap into the tube, one of the probes terminating near the top and the other near the bottom of the tube. Each probe is provided with a jack included on the cap, and a pair of cables, wired to an electronic timer and circuit board, are inserted in the jack. The base seal of the outflow meter is placed on the pavement surface and the tube is filled with water to a level exceeding the bottom end of the top brass probe, immersion of which prevents timer activation. After the discharge opening is unsealed and the water level in the tube drops below the level of the uppermost brass probe, the timer is activated. As the water level drops below the lowermost probe, the timer is stopped and the time required for the water level to drop from the uppermost probe to the lowermost probe, displayed on the timer, reveals the drainage characteristics of the pavement surface. However, this type of outflow meter is cumbersome to use, since care must be exercised to prevent the water from the tube from contacting the cable pins and jacks on the tube top, in order to prevent an electrical short and accompanying erroneous readings on the timer. The new and improved, self-contained outflow meter of this invention utilizes a pair of float switches having switch floats which are provided on upper and lower adaptors, respectively, in place of the brass probes of the conventional outflow meter. Because the upper and lower adaptors of the outflow meter are wired directly to the electronic timer, the need for a cable trailing from the adaptors to the electronic timer and circuit board is eliminated, also eliminating the need for exercising special care in preventing water in the tube from contacting the cable pins and jacks. Another outflow meter for measuring surface drainage characteristics of pavement is detailed in U.S. Pat. No. 4,070,903, dated Jan. 31, 1978, to Geoffrey Lees, et al, entitled "Outflow Meter For Measuring Surface Drainage Characteristics". The outflow meter is characterized by a disk having a surface-engaging face which is disposed in contact with the surface being measured, an orifice extending through the disk and terminating at the surface-engaging face, a mechanism for pressing the disk into engagement with the surface under a predetermined load and a mechanism for supplying a predetermined volume of fluid through the orifice to the surface-engaging face.

An object of this invention is to provide a new and improved, self-contained and compact outflow meter for measuring the water drainage rate on pavement.

Another object of this invention is to provide a new and improved outflow meter for measuring the water drainage characteristics of pavement, which outflow meter is characterized by portability, reliability, low maintenance and easy use.

Still another object of this invention is to provide a new and improved outflow meter for measuring the surface drainage characteristics of water on pavement, which outflow meter is characterized by an elongated, vertical water discharge tube for momentarily holding a selected volume of water, a base and sealing ring provided on the bottom end of the tube for supporting the tube on the pavement surface and a cap sealed in the top end of the tube, a spring-loaded plunger for selectively sealing a discharge opening provided in the base, a timer provided on the cap and a pair of adaptors extending downwardly from the cap into the tube at different levels and wired to the timer, one of which adaptors terminates near the top and the other near the bottom of the tube. A switch element is mounted on each adaptor and water is added to the tube until the water level in the tube is located above the level of the switch. By operation of the plunger, water flows from the tube through the discharge opening onto the pavement and when the water level falls below the upper switch, operation of the timer is initiated. When the water level falls below the lower switch, this action stops the timer. The period of time required for the water level in the tube to decrease from the lowest level of the upper switch to the lowest level of the lower switch indicates the drainage characteristic of the pavement surface.

SUMMARY OF THE INVENTION

These and other objects of the invention are provided in a new and improved outflow meter characterized by a

3 transparent water containment and discharge tube having a base sealed on or in the bottom end thereof for supporting the tube in upward-standing relationship on a pavement surface. An electronic timer and circuit are provided on a top or cap sealed on or in the upper end of the tube and a spring-loaded plunger is suspended in the tube from the cap and operates to selectively and reversibly seal the discharge opening in the base by hand pressure. In a most preferred embodiment, an upper adaptor having a vertically-displaceable switch float mounted thereon, extends downwardly into the tube interior and terminates near the top of the tube and a lower adaptor extends downwardly into the tube to a point near the bottom of the tube and includes a similar switch float mounted thereon. Both adaptors are wired to the timer. As water is poured through a cap opening provided in the cap while the plunger is in the sealing position in the base against spring bias and the water level rises to the level of the upper float, displacement of the floats upwardly on the adaptors, respectively, prevents operation of the electronic timer. Since the outflow meter has been placed with the bottom sealing ring on the pavement surface to be measured, release of the plunger from the discharge opening in the base allows water to drain from the tube onto the pavement. As the water level drops below the level of the upper float, downward movement of the upper float by gravity activates the timer and as the water level drops below the level of the lower float, downward movement of the lower float by gravity on the adaptor terminates operation of the timer. The time required for the water level to drop in the tube from the level of the upper float switch to the level of the lower float switch is proportional to the drainage characteristics of the pavement surface upon which the outflow meter is placed.

BRIEF DESCRIPTION OF THE DRAWINGS

The invention will be better understood by reference to the accompanying drawing, wherein:

FIG. 1 is a top view of a preferred embodiment of the outflow meter of this invention;

FIG. 2 is a bottom view of the outflow meter illustrated in FIG. 1;

FIG. 5 is a front view of the outflow meter filled with water;

FIG. 6 is a front view of the outflow meter in operating configuration; and

FIG. 7 is left side view of the outflow meter being filled with water.

DESCRIPTION OF THE PREFERRED EMBODIMENTS

Figure 3:
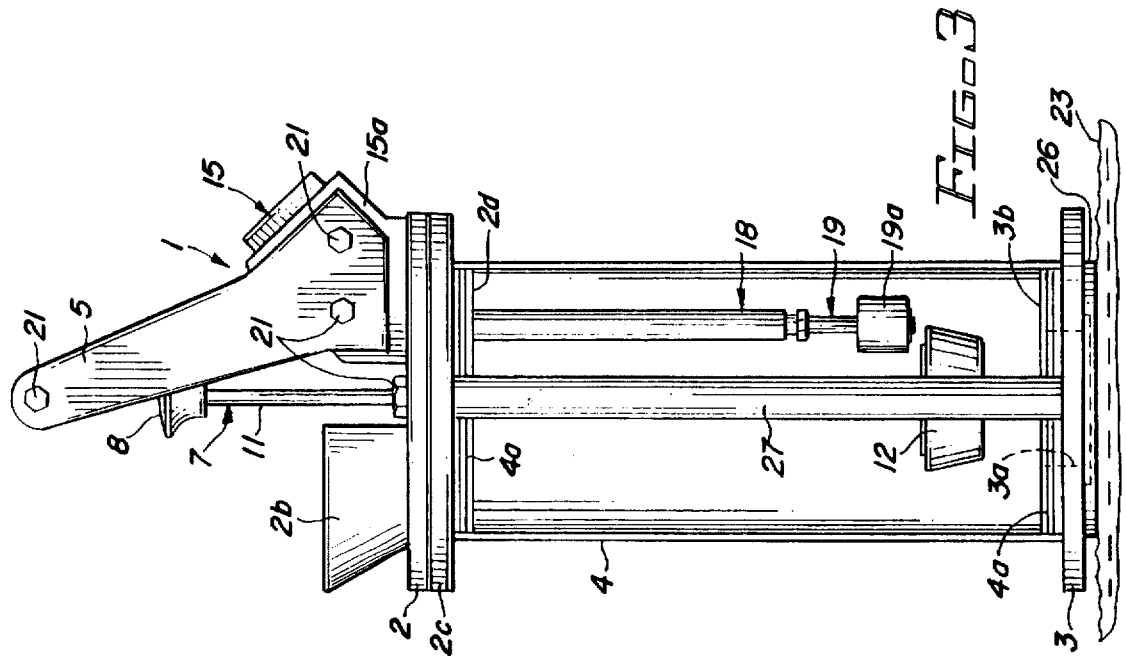
FIG. 3 is a left side view of the outflow meter illustrated in FIGS. 1 and 2, without water.
Figure 4:
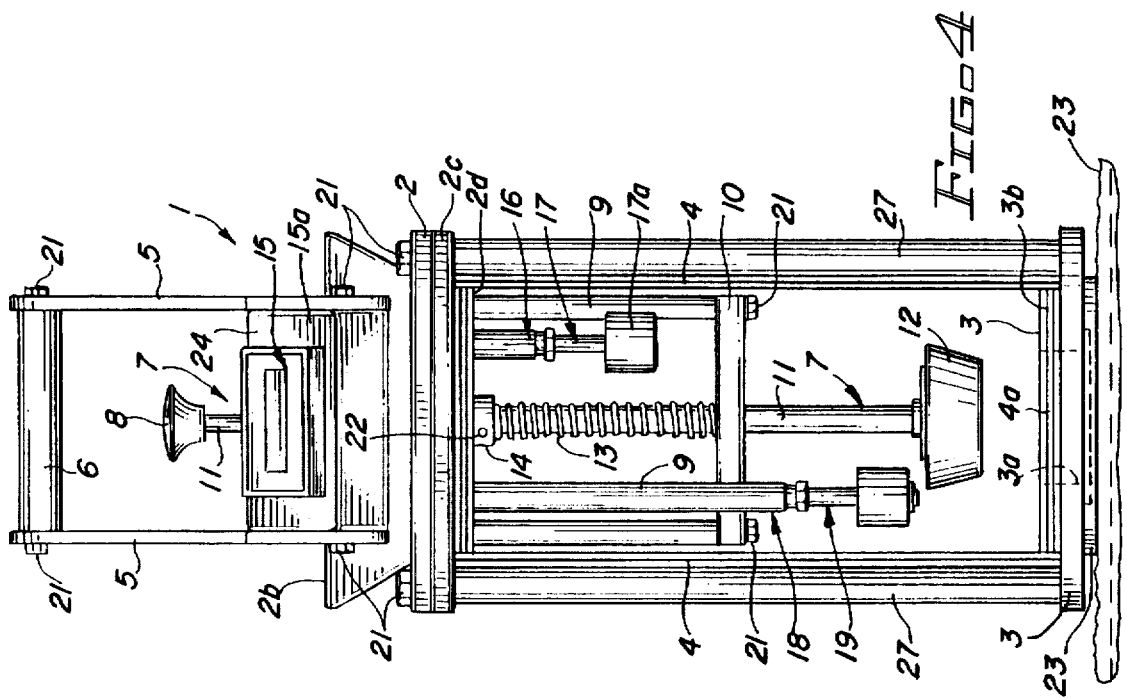
FIG. 4 is a front view of the empty outflow meter illustrated in FIG. 3.

Referring initially to FIGS. 1–4 and 7 of the drawings, in a preferred embodiment the outflow meter of this invention is generally illustrated by reference numeral 1. The outflow meter 1 is characterized by an elongated, generally cylindrical, vertically-oriented, preferably transparent water discharge tube 4, having a circular base 3, which is mounted in one end of the tube at a base flange 3b by means of an O-ring 4a. A circular discharge opening 3a is provided centrally in the base 3 and base flange 3b and a sealing ring 26 is provided on the bottom surface of the base 3, generally concentric with the discharge opening 3a. A circular top or cap 2 is mounted on a cap seat 2c, having a cap seat flange 2d, on the top end of the water discharge tube 4, by means of a pair of bolts 21, that seat in the upper end of two cap supports 27, which extend to the base 3. A pair of cap screws 28 mount the base 3 on the respective cap supports 27, as illustrated in FIG. 2. The top end of the water discharge tube 4 is sealed on the cap seat flange 2d of the cap seat 2c by means of a second O-ring 4a. A timer support 15a is welded on or formed in the upper surface of the cap 2 and an electronic timer 15 is mounted on the timer support 15a. A pair of handle brackets 5 extend upwardly from attachment by means of bolts 21 to each end of the timer support 15a and a handle 6 spans the upper ends of the handle brackets 5 and is attached thereto by additional bolts 21. As illustrated in FIGS. 1, 3 and 4, a cap funnel 2b is formed in the cap 2 and a cap opening 2a is formed in the cap 2 in the bottom of the cap funnel 2b to facilitate pouring water 29 into the water discharge tube 4 from a container 30, as illustrated in FIG. 5 and hereinafter further described. As further illustrated in FIGS. 3 and 4, a plunger 7 includes a plunger handle 8 on one end and a pair of plunger supports 9, each extending downwardly from the cap seat 2c, into the water discharge tube 4. A plunger guide 10 horizontally spans the lower ends of the plunger supports 9 and is secured by bolts 21. An elongated plunger rod 11 extends downwardly through a bearing (not illustrated) provided in the cap 2 and cap seat 2c, through an aligned opening (not illustrated) provided in the plunger guide 10. A plunger stop collar 14 is mounted on the plunger rod 11 below the cap 2 by means of a set screw 22. A plunger return spring 13 is provided on the plunger rod 11 and is secured in place between the plunger stop collar 14 and the plunger guide 10, as illustrated in FIG. 4. A tapered rubber plunger head 12 is mounted on the bottom end of the plunger rod 11 for reversibly sealing the discharge opening 3a provided in the base 3, as hereinafter further described. An elongated upper adaptor 16 extends downwardly from the cap seat flange 2d into the interior of the water discharge tube 4 and terminates near the upper end of the water discharge tube 4. In a most preferred embodiment of the invention an upper adaptor switch float 17a of an upper float switch 17 is vertically-slidably mounted on the lower end of the upper adaptor 16. An elongated lower adaptor 18 extends downwardly from the cap seat flange 2d into the interior of the water discharge tube 4, terminating near the bottom end of the water discharge tube 4 and includes a lower adaptor switch float 19a, vertically-slidably mounted on a lower adaptor float switch 19, provided on the end of the lower adaptor 18. The upper adaptor float switch 17 and lower adaptor float switch 19 are wired to the timer 15 (provided on the timer support 15a of the cap 2) in conventional manner, to activate and disactivate the upper adaptor float switch 17 and lower adaptor float switch 19, respectively. The pair of diametrically-opposed cap supports 27, extending between the cap 2 and the base 3, function to stabilize the cap 2 on the upper end of the water discharge tube 4. Alternatively, various contact switches which may be activated in sequence by the falling water level in the water discharge tube 4 may be used, according to the knowledge of those skilled in the art.

Referring again to FIGS. 1–4 and to FIGS. 5–7 of the drawings, the outflow meter 1 is used to measure the rate of water drainage on a pavement surface 23, in the following manner. The outflow meter 1 is first placed on the pavement surface 23 with the sealing ring 26 located under the base 3, resting firmly on the pavement surface 23. The plunger head 12 of the plunger 7 is then engaged with the discharge opening 3a provided in the base 3, by firmly depressing the plunger handle 8 by hand, as illustrated in FIG. 7. Water 29 is then poured from a container 30 into the top and bottom-sealed water discharge tube 4, through the cap funnel 2b and cap opening 2a, until the water level is above the upper adaptor float switch 17 and causes upper displacement of the upper adaptor switch float 17a and lower adaptor switch float 19a on the upper adaptor 16 and lower adaptor 18, respectively, as illustrated in FIG. 5. This position of the upper adaptor switch float 17a and lower adaptor switch float 19a opens the upper adaptor float switch 17 and lower adaptor switch float 19 and renders the timer 15 inoperable. The timer 15 is then activated by pressing a timer button (not illustrated) provided on the timer and the plunger head 12 is removed from the discharge opening 3a with the help of the plunger return spring 13, by releasing hand pressure on the plunger handle 8 of the plunger 7. This allows water to flow from the water discharge tube 4 through the discharge opening 3a and between the sealing ring 26 and pavement surface. As the water level falls below the level of the upper adaptor float switch 17, the floating upper adaptor switch float 17a moves downwardly on the upper adaptor 16 by gravity, closes the upper adaptor float switch 17 and causes the timer 15 to begin counting. When the water level falls below the level of the lower adaptor float switch 19, the floating lower adaptor switch float 19a likewise moves downwardly, displaced by gravity on the lower adaptor 18 and opens the lower adaptor float switch 19, to terminate operation of the timer 15. The time required for the water level to fall from the level of the upper adaptor float switch 17 to the level of the lower adaptor float switch 19 is indicated on the timer 15 and is proportional to the drainage characteristics of the pavement surface.

While the preferred embodiments of the invention have been described, it will understood and recognized that various modifications may be made in the invention and the appended claims are intended to cover all such modifications which may fall within the spirit and scope of the invention.

Having described my invention with the particularity set forth above, what is claimed is:

1. An outflow meter for resting on a pavement surface and measuring the time of drainage of water from the pavement, comprising a generally elongated, cylindrical water discharge tube having an upper filling end and a lower discharge end for containing a selected volume of water; base means sealingly mounted in said discharge end for supporting said water discharge tube in upstanding relationship on the pavement surface and having a discharge opening generally concentric with said discharge end for discharging water from said discharge tube; seal means carried by said base for resting on the pavement surface; cap means sealingly mounted on the upper end of said water discharge tube for sealing said upper end of said water discharge tube and a pair of substantially diametrically-opposed supports extending between said base means and said cap means for stabilizing said cap means on said water discharge tube; an electronic timer carried by said cap means for measuring the time of said discharging water; plunger means suspended from said cap means into said water discharge tube for reversibly sealing said discharge opening; a first float support mounted in said water discharge tube and a first float slidably mounted on said first float support adjacent to said discharge end of said water discharge tube; and a second float support mounted in said tube means and a second float mounted on said second float support adjacent to said upper end of said water discharge tube, whereby gravity displacement of said second float on said second float support responsive to said discharging water starts said timer and gravity displacement of said first float on said first float support responsive to said discharging water stops said timer.

2. The outflow meter of claim 1 comprising handle means mounted on said cap means for carrying and positioning said outflow meter on the pavement surface.

3. The outflow meter of claim 2 comprising funnel means shaped in said cap means for pouring the water in said tube means.

4. An outflow meter for resting on a pavement surface and measuring the water drainage rate of the pavement, comprising a generally elongated, cylindrical water discharge tube for containing a selected volume of water; a circular base sealingly mounted in said discharge end for supporting said water discharge tube in upward-standing relationship on the pavement surface and having a discharge opening generally concentric with said discharge end for discharging water from said water discharge tube; a rubber gasket carried by said base for resting on the pavement surface; a circular cap having a cap opening for receiving said water, said cap sealingly mounted on said water discharge tube; a pair of substantially diametrically-opposed supports extending between said base and said cap for stabilizing said cap on said water discharge tube; an electronic timer mounted on said cap for timing said discharging water; a handle mounted on said cap for carrying and positioning said outflow meter on the pavement surface; a plunger suspended from said cap into said water discharge tube and a plunger head provided on said plunger for reversibly sealing said discharge opening; a first float support extending downwardly from said cap into said water discharge tube and a first float slidably mounted on said first float support adjacent to said discharge end of said water discharge tube; and a second float support extending downwardly from said cap into said water discharge tube and a second float slidably mounted on said second float support adjacent to said top end of said water discharge tube, whereby upper displacement of said first float and said second float on said first float support and second float support, respectively, prevents operation of said timer and lower displacement of said second float and said first float on said second float support and said first float support, respectively, starts and stops said timer.

* * * * *